(12) United States Patent
He et al.

(10) Patent No.: US 8,329,990 B2
(45) Date of Patent: Dec. 11, 2012

(54) CROP GRAIN FILLING GENE GIF1 AND THE APPLICATIONS THEREOF

(75) Inventors: Zuhua He, Shanghai (CN); Ertao Wang, Shanghai (CN); Qun Li, Shanghai (CN)

(73) Assignee: Shanghai Institutes for Biological Sciences, Chinese Academy of Sciences, Shanghai (CN)

(*) Notice: Subject to any disclaimer, the term of this patent is extended or adjusted under 35 U.S.C. 154(b) by 393 days.

(21) Appl. No.: 12/312,235

(22) PCT Filed: Oct. 30, 2007

(86) PCT No.: PCT/CN2007/070984
§ 371 (c)(1),
(2), (4) Date: May 20, 2009

(87) PCT Pub. No.: WO2008/052478
PCT Pub. Date: May 8, 2008

(65) Prior Publication Data
US 2010/0064385 A1    Mar. 11, 2010

(30) Foreign Application Priority Data

Oct. 30, 2006 (CN) .......................... 2006 1 0117721

(51) Int. Cl.
*A01H 5/00* (2006.01)
*C12N 15/82* (2006.01)
(52) U.S. Cl. .................... 800/284; 800/298; 800/320
(58) Field of Classification Search .................. None
See application file for complete search history.

(56) References Cited

U.S. PATENT DOCUMENTS

| 6,383,776 B1 | 5/2002 | Allen et al. |
| 2003/0217387 A1 | 11/2003 | Tomes et al. |

FOREIGN PATENT DOCUMENTS

| WO | 03/008540 A2 | 1/2003 |
| WO | WO-03000905 A2 | 1/2003 |

OTHER PUBLICATIONS

Extended European Search Report and Written Opinion dated May 17, 2010, issued by the European Patent Office in European Patent Application No. EP-07817175.8 (7 pages).

First Official Report issued Nov. 19, 2010, by the Australian Patent Office in related Australian Patent Application No. 2007315473 (2 pages).

Cho, Jung-II, et al., "Molecular closing and expression analysis of the cell-wall invertase gene family in rice (*Oryza sativa* L.)"; Plant Cell Report (2005) vol. 24, No. 4, Jun. 1, 2005; XP019335476, ISSN: 1432-203X; pp. 225-236.

Ji, X.M., et al., "Tissue-specific expression and drought responsiveness of cell-wall invertase genes of rice at flowering"; Plant Molecular Biology, Journal of Molecular Evolution, vol. 59, No. 6, Dec. 1, 2005; XP019262811, ISSN: 1573-5028; pp. 950-953.

Ji, Xuemei, et al., Structure, Evolution, and Expression of the Two Invertase Gene Families of Rice; Journal of Molecular Evolution, vol. 60, No. 5, May 2005; XP019363207, ISSN: 0022-2844; pp. 615-634.

Chourey, Prem S., et al., "Genetic control of cell wall invertases in developing endosperm of maize"; Planta: An International Journal of Plant Biology, vol. 223, No. 2, Jan. 1, 2006; XP019344445, ISSN: 1432-2048; pp. 159-167.

International Search Report for PCT/CN2007/070984 mailed Feb. 14, 2008 (8 pages).

PCT International Preliminary Report on Patentability (IPRP) issued May 5, 2009, by the International Bureau of WIPO in International Application No. PCT/CN2007/070984 filed Oct. 30, 2007 (4 pages).

Office Action dated May 10, 2011, issued by the Canadian Intellectual Property Office in Related Canadian Patent Application No. 2,668,041 (3 pages).

EPO Communication (Office Action) dated Mar. 22, 2011, from the European Patent Office, in corresponding European Patent Application No. 07 817 175.8 (7 pages).

INV2_ORYSJ EMBL-EBI databases, Oct. 3, 2006, [online], [retrieved on Jan. 29, 2008] (2pages).

081118_WHEAT EMBL-EBI databases, Nov. 1, 1998 [online], [retrieved on Jan. 29, 2008] (1 page).

Q8GT5O_HORVU EMBL-EBI databases, Mar. 1, 2003, [online], [retrieved on Jan. 29, 2008] (1 page).

INV1_DAUCA EMBL-EBI databases, Aug. 1, 1992 [online], [retrieved on Jan. 29, 2008] (1 page).

Database Geneseq [online] Jun. 2, 2005 [Jun. 2, 2005], "Rice stress-regulated promoter SEQ ID No. 15304"; XP002564541, retrieved from EBI accession No. GSN: ACL36741, Database accession No. ACL36741 (2 pages).

Summary of Office Action dated Jan. 3, 2012, issued by the Mexican Patent Office in related Mexican Patent Application No. MX/a/2009/004809 (2 pages).

*Primary Examiner* — Elizabeth McElwain
(74) *Attorney, Agent, or Firm* — Osha Liang LLP

(57) ABSTRACT

A novel crop grain filling gene (GIF1) and the applications thereof are presented in the invention. The GIF1 gene can be applied to control grain filling, enhance crop yield or quality, or improve disease resistance or storage stability of crop grains. A method for improving crops is also presented in the invention. The GIF1 gene shows valuable potentials in controlling crop yield, quality, storage, and resistance to diseases.

8 Claims, 6 Drawing Sheets

US 8,329,990 B2

CROP GRAIN FILLING GENE GIF1 AND THE APPLICATIONS THEREOF

TECHNICAL FIELD

This invention relates to gene technology and botany field; particularly, relates to a novel crop grain filling gene, GIF1 (Grain Incomplete Filling 1) gene, and its applications.

BACKGROUND ART

Currently, investigations concerning the improvement of crop yield are mainly focused on the following aspects: 1. increasing crop sources, viz. improving crop photosynthesis; 2. elevating the sink volume; and, 3. enhancing the transport ability of photosynthate from source to sink. Among them, elevation in the sink volume and enhancement of transport ability of photosynthate from source to sink are effective breeding approaches.

Several approaches have been adopted to enhance crop yield and modify the crops. However, there still lacks effective means. With respect to rice, the major cereal crops of China, grain incomplete filling is present in many high yield varieties, especially in super hybrid rice and rice varieties with large ear and large grain, and greatly affects the improvement in the rice yield.

Therefore, it is highly necessary to search for an effective approach in the field to solve the problem of grain incomplete filling, thus further modifying the crops and enhancing the crop yield as well as crop quality.

CONTENTS OF THE INVENTION

The object of the present invention is to provide a novel crop grain filling gene, GIF1 (Grain Incomplete Filling 1) gene, and its applications.

In the first aspect of the invention, an isolated crop grain filling protein is presented, wherein the protein is selected from a group consisting of:

(a) a polypeptide having the amino acid sequence of SEQ ID NO: 2; or (b) a polypeptide derived from the polypeptide of (a) with one or more amino acid residues in SEQ ID NO:2 being substituted, deleted or added, and capable of promoting grain filling.

In the second aspect of the invention, an isolated polynucleotide is presented, wherein the polynucleotide is selected from:

(i) a polynucleotide that encodes the grain filling protein; or (ii) a polynucleotide complementary with the polynucleotide of (i).

In another preferred embodiment, the polynucleotide encodes the polypeptide having SEQ ID NO: 2.

In another preferred embodiment, the sequence of the polynucleotide is selected from:

(1) a nucleotide sequence of SEQ ID NO: 1;

(2) a nucleotide sequence of SEQ ID NO: 3; or (3) a nucleotide sequence complementary to any one of the nucleotide sequence of (1) or (2).

In the third aspect of the invention, a vector is presented, wherein the vector contains said polynucleotide.

In the fourth aspect of the invention, a genetically engineered host cell is presented, wherein the cell contains said vector or the cell genome is integrated with said polynucleotide.

In the fifth aspect of the invention, a use of the grain filling protein or its encoding gene is presented, which comprises:

regulating grain filling (preferably facilitating crop grain filling);

regulating sugar metabolism or accumulation involved in crop grains; or improving the disease tolerance and storage stability of crop grains.

In the sixth aspect of the invention, a method for modifying crops was presented, which comprises:

increasing the expression of said grain filling gene in the crop.

In the seventh aspect of the invention, a method for preparing transgenic plants was presented, which comprises the step of:

introducing the polynucleotide of the present application into plant cells or tissues, culturing said plant cells or tissues, and regenerating said plant cells or tissues to plants.

In another preferred embodiment of the invention, the method comprises the steps of:

(a) providing *Agrobacterium tumefaciens* carrying the expression vector, wherein the expression vector comprises the encoding gene for the grain filling protein;

(b) contacting crop cells, tissues or organs with the *Agrobacterium tumefaciens* in step (a) so as to introduce the DNA sequence encoding grain filling protein into said crop cells, tissues or organs, and integrate the same into the crop chromosome;

(c) regenerating the crop cells, tissues or organs introduced with the DNA sequence encoding grain filling protein to crop plants.

In the eighth aspect of the invention, an agonist or antagonist for the grain filling protein or its encoding gene is presented.

Other aspects of the invention will be readily apparent to those skilled in the art based on the contents contained in the invention.

BRIEF DESCRIPTION OF THE FIGURES

FIG. 1B refers to brown rice grains of mutant plant; FIG. 1C refers to polished rice grains of wild-type plant; and FIG. 1D refers to polished rice grains of mutant plant.

FIG. 4B and FIG. 4D (magnification of FIG. 4B) refer to the isolated *Alternaria* sp.

MODE OF CARRYING OUT THE INVENTION

Figure 1:
FIG. 1 shows the effect of GIF1 gene on rice quality, wherein FIG. 1A refers to brown rice grains of wild-type plant.

During our deep research, the inventors for the first time discovered a novel gene controlling crop grain filling. Non-expression or lowered expression of the gene would significantly interfere with crop grain filling and reduce seed weight. Comparatively, enhanced expression of the gene could facilitate crop grain filling and increase seed weight. The gene was cloned through fine mapping, and was named as GIF1 (Grain Incomplete Filling 1). Investigations confirmed that normal expression of GIF1 in wild-type plant led to normal growth of crop grains, while mutation of GIF1 causing nonexpression of the GIF1 protein would result in poor rice quality, low seed vigor, and poor resistance towards storage diseases. Besides, the above features were notably improved in transgenic crops with additional GIF1 in relation to enhanced expression of GIF1 protein. Based on the aforementioned investigations, the current invention has been completed.

As used herein, "crop" refers to, but not limited to, Gramineous plants. Preferably, Gramineous plants includes, but not limited to, rice, wheat, barley, maize, broomcorn, etc.

As used herein, the term "isolated" refers to a substance which has been isolated from the original environment. For naturally occurring substance, the original environment is the natural environment. e.g., the polynucleotide and polypeptide in a naturally occurring state in the viable cells are not isolated or purified. However, if the same polynucleotide and polypeptide have been isolated from other components naturally accompanying them, they are isolated or purified.

As used herein, "isolated GIF1 protein" or "isolated GIF1 polypeptide" refers to the GIF1 protein that does not exist in the natural environment, which includes completely purified GIF1 protein. Substantively purified GIF1 protein contains almost no naturally relevant protein, lipid, saccharide, or other substances. The GIF1 protein could be purified by those skilled in the art using standard protein purification techniques. Essentially purified polypeptide forms a single main band on a non-reductive PAGE gel.

Polypeptides of the present invention can be recombinant polypeptide, natural polypeptide, or synthetic polypeptide, preferably recombinant polypeptide. Polypeptides of the present invention may be a purified natural product or a chemically synthetic product. Alternatively, it may be produced from prokaryotic or eukaryotic hosts, such as bacteria, yeast, higher plant, insect, and mammalian cells, using recombinant techniques. According to the host used in the recombinant production, the polypeptide may be glycosylated or non-glycosylated. Polypeptides of the present invention could bear or not bear the initial methionine residue.

The invention further comprises the fragments, derivatives and analogues of GIF1. As used in the invention, the terms "fragment", "derivative" and "analogue" mean the polypeptide that essentially retains the same biological functions or activity of GIF1 protein. Based on the following descriptions and examples, one having ordinary skill in the art could easily determine whether the polypeptide have the same biological functions or activities as the GIF1 protein. Polypeptide fragment, derivative or analogue of the present invention could be (i) a polypeptide with one or more conserved or non-conserved amino acid residue (preferably conserved amino acid residue) being substituted, wherein the substituted amino acid residue could be encoded or not encoded by the genetic code; or (ii) a polypeptide with one or more amino acid residues including substituted groups; or (iii) one in which the mature polypeptide is fused with another compound, such as a compound to increase the half-life of the polypeptide (for example, polyethylene glycol), or (iv) one in which the additional amino acids, such as a leader or secretary sequence or a sequence used for purifying polypeptide or pro-protein, are fused to the polypeptide. Such fragments, derivatives and analogs are known to the artisans based on the teachings herein.

As used herein, the term "GIF1 protein" refers to a polypeptide with the amino acid sequence of SEQ ID NO: 2 and GIF1 protein activity. The term also comprises the variants which have the same function of GIF1 protein and have the amino acid sequence of SEQ ID NO: 2. The variants includes, but not limited to, deletions, insertions and/or substitutions of several (typically 1-50, preferably 1-30, more preferably 1-20, most preferably 1-10, still preferably 1-8 or 1-5) amino acids, and addition of one or more (typically less than 20, preferably less than 10, more preferably less than 5) amino acids at the C-terminal and/or N-terminal. For example, protein function is usually unaltered in the art when substituted with amino acids of similar or analogous characteristics. Besides, protein function is usually unaltered following addition of one or more amino acids at the C-terminal and/or N-terminal, either. The term also includes the active fragments and active derivatives of GIF1 protein.

The variants of polypeptide include homologous sequences, conservative mutants, allelic variants, natural mutants, induced mutants, proteins encoded by DNA which hybridizes to GIF1 DNA under high or low stringency conditions, as well as the polypeptides retrieved by antisera raised against GIF1 polypeptide. The invention also provides other polypeptides, e.g. fusion protein containing GIF1 protein or fragment thereof. Apart from the substantially full-length polypeptide, the invention also includes the soluble fragments of GIF1 protein. Usually, such fragments comprise at least about 20, typically at lease about 30, preferably at least about 50, more preferably at least about 80, and most preferably about 100 continuous amino acids of the GIF1 sequence.

The invention also provides the analogues of GIF1 protein or polypeptide. Difference between the analogue and natural GIF1 could be the amino acid sequence, the modification mode which does not affect the sequence, or by both. These polypeptides include natural or induced genetic variants. Induced variant could be prepared by various techniques including random mutagenesis induced by irradiation or exposure to mutagens, site-directed mutagenesis or other known molecular biology techniques. Analogues also include the analogues containing amino acids different to the natural L-amino acid residues (e.g. D-amino acid), or unnatural or synthetic amino acids (e.g. ($\beta$-, $\gamma$-amino acid). It should be understood that polypeptides in the invention are not limited to the aforementioned typical polypeptides.

Modifications (usually the primary structure being unaltered) include in vivo or in vitro chemical derivatives of the polypeptide, such as acetylation or carboxylation. Modifications also include glycosylation. Modification also includes sequence of phosphorylated amino acid residues (e.g. phosphotyrosine, phosphoserine, and phosphothreonine). It also includes modified polypeptides with improved resistance to proteolytic hydrolysis and optimized solubility.

In the invention, "conserved variants of GIF1 protein" refers to a polypeptide with at most 20, preferably at most 10, more preferably at most 5, most preferably at most 3 amino acids being substituted with amino acids having substantially the same or similar property. These conserved variants are preferably obtained according the amino acid substitution as listed in Table 1.

TABLE 1

| Amino acid residue | Typical substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |

TABLE 1-continued

| Amino acid residue | Typical substitution | Preferred substitution |
|---|---|---|
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The invention also provides the polynucleotide sequence that encodes the GIF1 protein of the present invention or the conserved variants thereof.

The polynucleotide may be in the form of DNA or RNA. DNA includes cDNA, genomic DNA or synthetic DNA. DNA may be single-stranded or double-stranded. DNA may be a coding strand or a non-coding strand. Sequence of the coding region that encodes mature polypeptide may be the same as in ID NO: 1 or SEQ ID NO: 3, or is a degenerate variant. As used herein, "degenerate variant" refers to a nucleic acid sequence encoding a protein of SEQ ID NO: 2, and which is different from the sequence of the coding region as shown in SEQ ID NO: 1 or SEQ ID NO: 3.

Polynucleotides encoding the mature polypeptide of SEQ ID NO:2 include those only encoding mature polypeptide; those encoding mature polypeptide and various additional encoding sequences; those encoding mature polypeptide (and optional additional encoding sequence) and non-encoding sequence.

The term "polynucleotide encoding the polypeptide" may be the polynucleotide that encodes the polypeptide. It may also include polynucleotide of additional encoding sequence and/or non-encoding sequence.

The invention also relates to the variants of the aforementioned polynucleotide, encoding the polypeptide having the same amino acid sequence as described herein, or its fragment, analogue, and derivative. The variants of the polynucleotide may be naturally occurring allelic variant or non-naturally occurring variant. Such nucleotide variants include substitution variants, deletion variants, and insertion variants. As known in the art, allelic variant is the substituted form of the polynucleotide, within which one or more nucleotides may be substituted, deleted or inserted without substantially altering the function of the encoded polypeptide.

The invention also relates to polynucleotide that hybridizes with the aforementioned sequence, wherein the two sequences have a sequence identity of at least 50%, preferably at least 70%, more preferably at least 80%. The invention specifically relates to the polynucleotides that hybridize with the polynucleotide of the invention under stringent conditions. "Stringent conditions" used herein refers to (1) hybridization and elution at relatively low ionic strength and high temperature, such as 0.2×SSC, 0.1% SDS, and 60° C.; or (2) hybridization in the presence of denaturant, such as 50% (v/v) formamide, 0.1% calf serum/0.1% Ficoll, 42° C., etc; or (3) hybridization only when sequence identity between the two sequences was at least above 90%, preferably above 95%. In addition, the hybridizable polynucleotide encoded polypeptide shares the same biological function and activity as the mature polypeptide as shown by SEQ ID NO: 2.

The invention also relates to the nucleic acid fragment that hybridizes with the aforementioned sequence. As used herein, length of the "nucleic acid fragment" is at least 15 nucleotides, preferably at least 30 nucleotides, more preferably at least 50 nucleotides, most preferably at least 100 nucleotides. The nucleic acid fragment can be used in amplifying techniques of nucleic acid (e.g. PCR) to determine and/or isolate the GIF1 protein encoding polynucleotide.

It should be understood that although the GIF1 gene in the invention is obtained from rice, genes from other crops having high homology (e.g. above 80%, such as above 85%, 90%, 95%, even 90% sequence identity) with rice GIF1 gene are also included within the scope of the invention. Methods and tools for identifying the sequence homology are known in the art, such as BLAST. Following the discovery of rice GIF1 gene, the inventors succeeded in discovering highly homologous genes in other crops such as AF030420 gene in wheat, AJ534447 gene in barley, and X69321 gene in carrot, using BLAST. The applications of these highly homologous genes in crop grain filling, sugar metabolic regulation and accumulation, and crop improvement are also included within the protected scope of the invention.

Full-length sequence of the GIF1 nucleotide or its fragment can be prepared by PCR amplification, recombination or synthetic methods. For PCR amplification, one can obtain said sequences by designing primers based on the nucleotide sequence disclosed herein, especially the ORF, and using cDNA library commercially available or prepared by routine techniques in the art as a template. When the sequence is long, it is usually necessary to perform two or more PCR amplifications and link the amplified fragments together correctly.

Once the sequence is obtained, one can produce lots of the sequences by recombinant methods. Usually, said sequence is cloned into a vector which is then transformed into a host cell. The sequence is isolated from the amplified host cells using conventional techniques.

Further, the sequence can be synthesized, especially when the fragments are short. Typically, several small fragments are synthesized and linked together to obtain a long sequence.

It is completely feasible to chemically synthesize the DNA sequence encoding the protein of invention, or the fragments or derivatives thereof. The DNA sequence can thereafter be introduced into various available DNA molecules (or vectors) and cells in the art. In addition, mutation can be introduced into the protein sequence by chemical synthesis.

This invention also relates to the vector containing the polynucleotide of the invention, the host cells obtained from the vector or GIF1 encoding sequence of the invention via genetic engineering, and the method for obtaining the polypeptide of the invention using recombinant techniques.

Using conventional DNA recombinant techniques (Science, 1984; 224:1431), the polynucleotide sequence of the invention can be used to express or produce recombinant GIF1 protein. Generally, it comprises the following steps:

(1) transfecting or transforming appropriate host cells with the polynucleotide (or the variant) encoding GIF1 polypeptide or the vector containing the polynucleotide;

(2) culturing the host cells in an appropriate medium;

(3) isolating or purifying the protein from the medium or cells. The GIF1 polynucleotide sequence in the invention can be inserted into the recombinant expression vector. The term "recombinant expression vector" refers to a bacterium plasmid, phage, yeast plasmid, virus of plant cell, virus of mammalian cell or other vectors known in the art. Any plasmid or vector can be used as long as it is capable of replicating and is stable in the host. As an important characteristic, the expression vector usually contains origin of replication, promoter, marker gene and translation regulation element.

Methods known by those skilled in the art can be used for the construction of expression vectors containing the DNA sequence encoding GIF1 protein and proper transcription/translation regulation elements. These methods include in vitro recombinant DNA technique, DNA synthesis technique, in vivo recombinant technique and so on. The DNA sequence may be effectively linked to a proper promoter in the expression vector to direct the synthesis of mRNA. The expression vector also includes a ribosome binding site for initiating translation and a transcription terminator.

Furthermore, the expression vector preferably includes one or more selective marker gene, which provides a phenotype for selecting transformed host cells, such as dihydrofolate reductase, neomycin resistance, and green fluorescence protein (GFP) for eukaryotic cell culture, and kanamycin as well as ampicillin resistance for *E. coli*.

The vectors that contain aforementioned proper DNA sequence, promoter or regulation sequence can be transformed into appropriate host cells to express the protein.

The hose cells can be prokaryotic cells, such as bacterium cells; or lower eukaryotic cells, such as yeast cells; or higher eukaryotic cells, such as plant cells. Typical examples are *E. coli, Streptomyces, Agrobacterium tumefaciens*; fungus cells such as yeast; plant cells, etc.

When the polynucleotide of the invention is expressed in higher eukaryotic cells, insertion of enhancer sequence in the vector can enhance transcription. Enhancer is a DNA cis-acting element with about 10-300 bp, which acts on the promoter to enhance gene transcription.

Artisans in the art know clearly how to select proper vectors, promoters, enhancers and host cells.

Transformation of host cells with recombinant DNA may be performed using conventional techniques known to those skilled in the art. When the host is a prokaryote, such as *E. coli*, competent cells capable of DNA uptake, can be prepared from cells harvested after exponential growth phase and subsequently treated by the $CaCl_2$ method using known procedures. Another method includes the use of $MgCl_2$. Transformation can also be performed through electroporation when necessary. When the host is an eukaryote, DNA transfection methods including calcium phosphate co-precipitation, conventional mechanical methods such as microinjection, electroporation, or liposome encapsulation, may be used. Plant transformation may also use the method of *Agrobacterium tumefaciens* transformation or particle gun transformation, such as the leaf disc method, rice immature embryo transformation method, etc. Transformed plant cells, tissues and organs can be regenerated to plants to obtain a plant with improved grain filling ability or grain quality.

The obtained transformants are cultured using conventional methods to express the polypeptide encoded by the gene of the invention. Culture medium may be selected from various conventional culture medium based on the host cells used. When the host cells have grown to a proper density, the selected promoter is induced using appropriate methods (such as temperature transformation or chemical induction), followed by incubation for an additional period of time.

The recombinant polypeptide in the aforementioned method may be expressed intracellularly or on the cell membrane, or secreted to the outside the cell. If necessary, the recombinant protein may be isolated and purified using various isolation techniques according to its physical, chemical or other characteristics. These techniques are known to those skilled in the art. Examples of the techniques includes, but not limited to, conventional renaturation treatment, treatment with protein precipitator (saltingout), centrifugation, cell lysis by osmosis, ultra-treatment, ultracentrifugation, size-exclusion chromatography (gel filtration), absorption chromatography, ion-exchange chromatography, high performance liquid chromatography (HPLC), other liquid chromatography techniques or a combination thereof.

The recombinant GIF1 protein or polypeptide may be subject to various applications, including screening of antibodies, polypeptides or other ligands that enhance or inhibit the GIF1 protein function. Screening polypeptide banks using expressed recombinant GIF1 protein can be used to find valuable polypeptide molecules that are capable of inhibiting or stimulating GIF1 protein function.

Polynucleotide of the invention may be partly or entirely fixed on a microassay or DNA chip (also termed as "gene chip") as a probe for the differential expression analysis of genes in tissues. Transcription product of GIF1 protein may also be tested by in vitro amplification of RT-PCR with GIF1 specific primers.

The invention also relates to a method for improving crops, wherein the method comprises enhancing the expression of GIF1 gene or its homologous genes in the crop.

The methods for enhancing the expression of GIF1 gene or its homologous genes are known to those skilled in the art, such as driving by strong promoters. Enhancer (such as the first intron of rice waxy gene, and the first intron of Actin gene) may be alternatively used to enhance the expression of GIF1 gene. Strong promoters suitable for the method of the invention include, but not limited to, 35s promoter, Ubi promoters of rice and maize, etc.

As a preferred embodiment of the invention, the method for improving crops comprises the followings steps:

(1) providing *Agrobacterium tumefaciens* harboring the expression vector, wherein the expression vector comprises a DNA sequence encoding GIF1 protein;

(2) contacting plant cells, tissues or organs with the *Agrobacterium tumefaciens* of step (1), to allow the transfection of said DNA sequence encoding GIF1 protein into the plant cells and the integration onto the host chromosome;

(3) selecting the plant cells or tissue transfected with the DNA sequence encoding GIF1 protein;

(4) regenerating the plant cells or tissues of step (3) to plants.

Any appropriate conventional means, including reagents, temperature, pressure condition, etc, may be used for the application of the method.

Moreover, the invention also relates to the application of the crop grain filling trait as the tracing label for transgenic plant offspring. Besides, the grain filling trait of said gene may also be applied as an indication label for the eu-hybrids during breeding by crossing.

In one example of the invention, a GIF1 gene having a genome sequence of 6840 by (SEQ ID NO: 3) was presented. The ORF was located at 2380-2594, 3723-4605, 4994-5152, 5903-6168, 6276-6364, 6651-6840, and the total cDNA (SEQ ID NO: 1) was 1797 bp, which encoded a protein (SEQ ID NO: 2) comprising 598 amino acids. The GIF1 gene can be used to provide novel approaches for improving crop varieties, and therefore exhibits a profound potential for practical application.

Advantages of the Present Invention Include:

(1) it is the first time to isolate and obtain a novel crop grain filling gene GIF1, which is capable of dominating grain filling and controlling crop quality.

(2) crop grain filling gene GIF1 serves as a gene for dominating crop grain filling and enhancing crop yield as well as quality, and is applied to varietal improvement.

The invention is further illustrated by the following examples. It is appreciated that these examples are only intended to illustrate the invention, but not to limit the scope of the invention. For the experimental methods in the following examples, they are performed under routine conditions, e.g., those described by Sambrook et. al., in Molecule Cloning: A Laboratory Manual, New York: Cold Spring Harbor Laboratory Press, 1989, methods reported in PCR Primer: A Laboratory Manual by Carl W. Dieffenbach and Gabriela S. Devksler eds. (Cold Spring Harbor Laboratory Press, 1995), or as instructed by the manufacturers, unless otherwise specified.

Materials and Methods:

1. Cloning and Transformation of pCAMBIA1301-GIF1

GIF1 was digested by restriction enzymes MunI and BamHI, and was thereafter ligated to BamHI and EcoRI digested pBluescript sk+ (Stratagene). The clone produced was further digested by Hind III and Bam HI, and was cloned to equally digested pCAMBIA1301 to obtain pCAMBIA1301-GIF1.

Transformation of pCAMBIA1301-GIF1 into *Agrobacterium tumefaciens* was carried out using the following protocol:

1. add 1 µg of pCAMBIA1301-GIF1 plasmid to competent cells of *Agrobacterium tumefaciens* EHA 105 (Hood, E. E., Gelvin, S. B., Melchers, L. S, and Hoekema, A., Transgenic Res., 1993, 2, 208-218) and incubate on ice for 30 min;

2. freeze the cells by liquid nitrogen for 1 min;

3. unthaw frozen cells in 37° C. water;

4. add 1 mL of YEP and incubate at 28° C. for 2-4 h;

5. spread 200 µl of the above suspension on antibiotics-containing YEP plates;

6. incubate for 2 days at 28° C. until positive colonies are observed and select the positive colonies.

2. Induction and Transformation of the Call of Rice Mature Embryos

Hulls of ZH11 and mutant (gif1) seeds were removed. The seeds were immersed in 70% ethanol for 1 min, and then in 20% (v/v) NaClO for 20 min with shaking. They were then washed with sterilized water for 5-6 times to yield ivory white grains without abnormal smell. Excessive water was blotted with aseptic filter paper, and the calli were induced on the NBD/N6 culture medium. After being cultured in dark at 26° C. for 1 week, the calli were peeled off, and the endosperm, embryo and radicel were removed.

The calli were subcultured in dark on the NBD/N6 culture medium (Sigma), and were passaged every 2-3 weeks as receptors.

3. *Agrobacterium*-Mediated Transformation of Rice Calli 1. inoculate the calli on the NBD/N6 medium, and incubate in dark at 25-26° C. for 4 days;

2. prepare YEB CM culture medium;

3. steak *Agrobacterium tumefaciens* EHA 105 containing the recombinant plasmid pCAMBIA1301-GIF1 on YEB medium (containing 50 ul/ml of Kan and 20 ug/ml of Rif), and culture the same at 28° C., 200 rpm for 36 h;

4. culture the bacteria until $OD_{660}$ reaches 1.0-1.5;

5. transfer the calli into a sterilized triangular flask;

6. pour proper amount of the above cultured *Agrobacterium tumefaciens* EHA105 into the flask and ensure that all the calli are immersed therein;

7. incubate at ambient temperature for 20 min with gentle shaking;

8. remove the bacterium suspension and blot excessive suspension using aseptic filter paper; transfer the calli onto the NBD culture medium (+AS 100);

9. co-culture at 20-25° C. for 2-3 days;

10. transfer the co-cultured calli into a sterilized triangularflask, wash the calli with sterilized water containing 500 mg/L carbenicillin for 2-3 time to remove the bacteria;

11. transfer the calli to the selective medium (containing NBD, 200 mg/L of Timent and 50 mg/L of hygromicin (Hyg)) for screening of transformed cells. Perform two to three screening cycles (3 weeks for each).

12. transfer the pre-differentiated calli to differential medium (containing NB, 2 mg/L of BAP, and 0.5 mg/L of NAA) after 2-3 week, incubate at 26° C. for 16 h with light and 8 h in dark.

13. transfer the resistance regenerated plant to root media (containing ½MS and 0.5 mg/L of NAA) after 2-3 weeks for strong seedling and rooting;

14. wash away the agar from the resistance regenerated plant after 3 weeks, transplant it to the greenhouse, and collect the seeds for molecular identification.

4. Quantification of sugar and starch Developing grains were harvested, immediately frozen in liquid nitrogen and stored at −80° C. until use. Sugar content and starch levels in grains without hulls were determined using the method by Hampp et al. (Hampp, R., Egger, B., Effenberger, S. & Einig, W. Carbon Allocation in Developing Spruce Needles—Enzymes and Intermediates of Sucrose Metabolism. Physiologia Plantarum 90, 299-306 (1994)).

Example 1

Population Construction, Gene Cloning and Function Analysis

The inventor discovered a rice mutant from the mutant bank induced from Zhonghua 11 (ZH11), wherein the seed filling of the mutant was seriously interfered. Vegetative growth of the mutant crop showed no significance to wild-type ones, while grain filling was significantly interfered with a decrease in the weight of 1,000 grains of 15-30% and a reduction in rice quality. It was then entitled gif1 (grain incomplete filling 1), which confirmed that the GIF1 gene was an important gene that controlled the crop yield and rice quality through grain filling.

The inventor obtained a gene mapping population through the hybridization between the gif1 mutant and Zhenshan 97. A scan for the LIF1 locus was performed through Bulked Segregant Analysis (BSA) using the 130 pairs of SSR primers uniformly distributed on the 12 rice chromosomes. The Lif1 locus was primarily mapped to be near the SRD5 region on the long arm of chromosome 4, and was ultimately mapped to a 32-kb fragment between caps-4 and caps-8 comprising three putative genes. The inventor discovered a 1-nt deletion in the gif1 mutant (nt 4588 on the DNA sequence of GIF1 genome) based on the DNA sequencing of the mutant and wild-type crops.

Through fine-mapping of GIF1, sequencing and function validation, the inventor obtained the genome sequence of wild-type GIF1 (DNA) as shown by SEQ ID NO: 3 (including promoter), the sequence of GIF1 coding region (cDNA sequence) as shown by SEQ ID NO: 1, and the protein sequence of GIF1 as shown by SEQ ID NO: 2.

In the case of the aforementioned mutation (deletion of the No. 4588 nucleotide in the genome sequence of GIF1), the mutant did not express GIF1 protein.

Example 2

Effect of GIF1 Gene on Grain Filling and Yield

The inventor compared various phenotypes of rice grains from gif1 mutant with those of GIF1 wild-type ZH11 crops. Results were shown in Table 2.

TABLE 2

Effect of gif1 mutant on rice grain phenotype

| | ZH11 | gif1 | gif1/ZH11 | Significance |
|---|---|---|---|---|
| Ear number/crop | 11.00 ± 2.30 | 9.96 ± 2.73 | 0.90 | no |
| Seed number/ear | 122.12 ± 33.71 | 124.82 ± 30.70 | 1.02 | no |
| Seed number/crop | 1343.29 ± 372.12 | 1279.38 ± 239.05 | 0.95 | no |
| Number of incomplete filling seed/ear | 35.56 ± 10.83 | 34.33 ± 15.68 | 0.97 | no |
| Seed weight (g)/ear | 2.90 ± 0.73 | 2.45 ± 0.63 | 0.84 | yes |
| Seed weight (g)/crop | 32.14 ± 8.60 | 25.09 ± 4.44 | 0.78 | yes |
| weight of 1,000 seeds (g) | 24.00 ± 0.01 | 19.71 ± 0.01 | 0.82 | yes |
| weight of 1,000 brown rice grains (g) | 21.33 ± 0.1 | 16.15 ± 0.15 | 0.76 | yes |

As illustrated in the Table, the gif1 mutant interfered with seed filling and reduced crop yield although ear number or seed number was not interfered. The results showed in following Example 3 demonstrated that transgenic complementation could effectively eliminate such interference and control rice grain filling, and thus increasing the crop yield.

Example 3

Effect of GIF1 Gene on Rice Quality

The grains of brown rice and polished rice having wild-type GIF1 gene were big and full, while those of the mutant rice without the expression of GIF1 gene were small and not full. The inventor constructed the recombinant plasmid of pCAMBIA1301-GIF1 containing GIF1 gene, and transformed the same to the mutant (gif1) calli. The mutant transgetic plant was thus obtained, which could regain the wild-type features.

Figure 7:
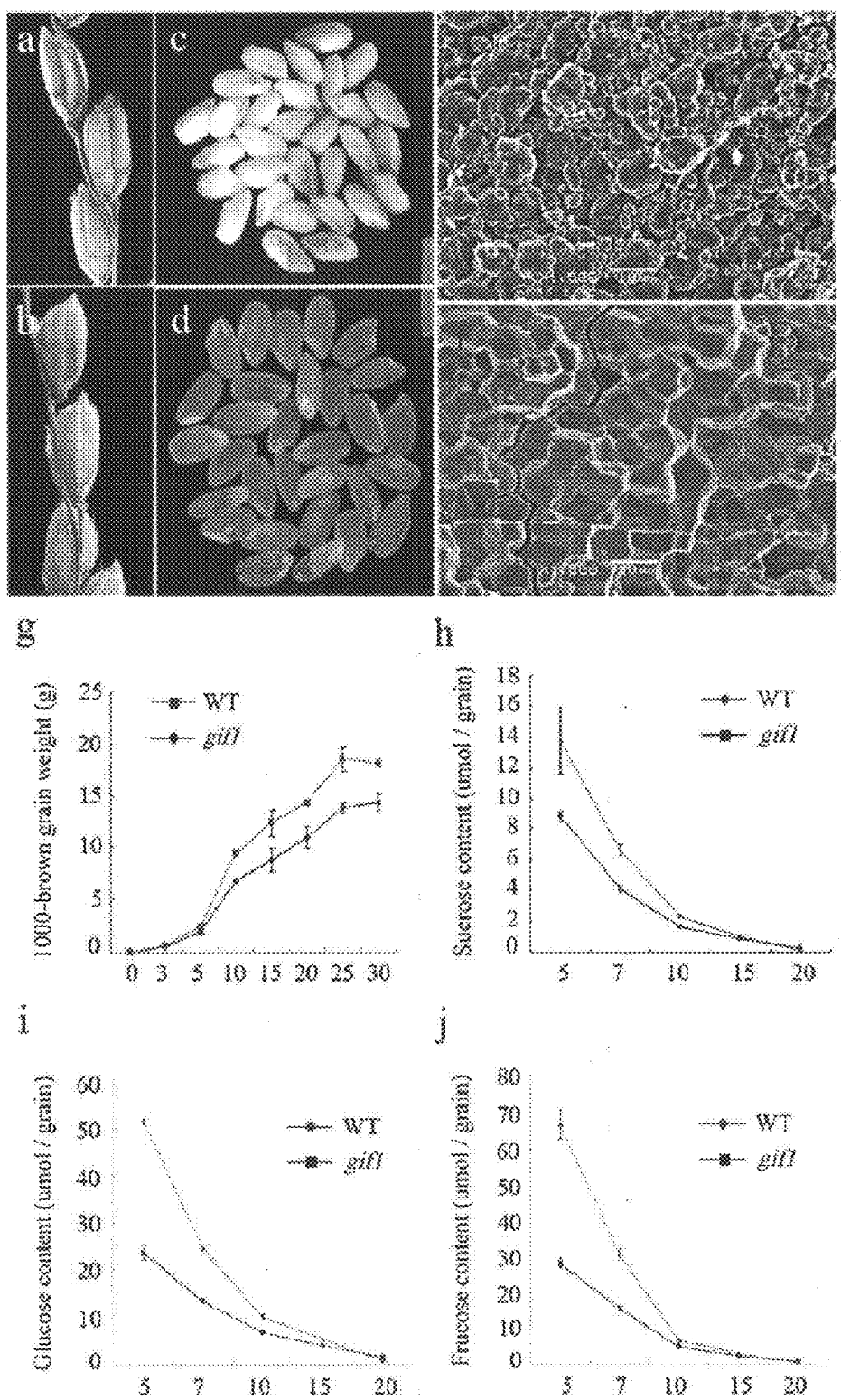
FIG. 7 shows grain-filling and sugar content of wild-type or gif1 mutant grains. (a) and (b) gif1 mutant grains (a) and wild-type grains (b) on 25DAF. (c) and (d) polished rice grains of gif1 mutant rice (c) and wild-type rice (d). (e) and (f) SEM analysis of gif1 mutant grains (e) and wild-type grains (f). Results show abnormal development and loosening of gif1 mutant starch granules. (g) grain filling process (1000-brown rice weight) of wild-type or gif1 mutant rice. (h)-(j) sucrose, sugar, and fructose contents in wild-type or gif1 mutant grains, respectively.

Results were shown in FIG. 1 and FIGS. 7(a-g). The grains of brown rice and polished rice having wild-type GIF1 gene were big and full, while those of mutant rice without the expression of GIF1 gene were small and not full.

Therefore, the mutant (gif1) reduced the rice quality, whereas transgenic complementation could effectively inhibit the reduction in rice quality as induced by the gif1 mutant and thereby improving the crop quality.

Figure 8:
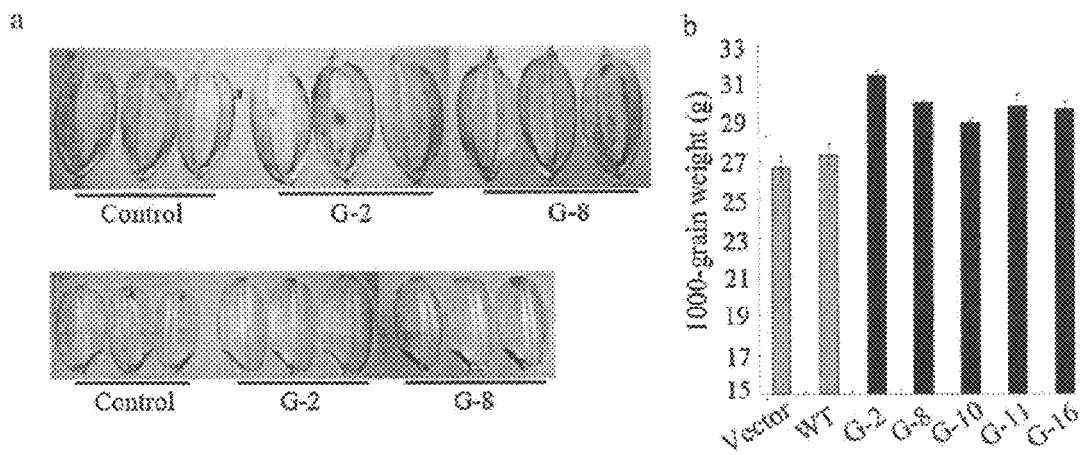
FIG. 8 shows the enlarged size of the grains of transgenic rice overexpressing GIF1. (a) Two transgenic rice lines, G-2 and G-8, overexpressing GIF1, are compared to control wild-type rice in terms of grain size. Results show that the transgenic rice lines possess larger grains. (b) comparison of grain weight among five transgenic rice lines overexpressing GIF1 (G-2, G-8, G-10, G11, and G-16), wild-type rice (WT), empty vector transformed rice (Vector). Statistically difference: *$P<0.05$.
Figure 9:
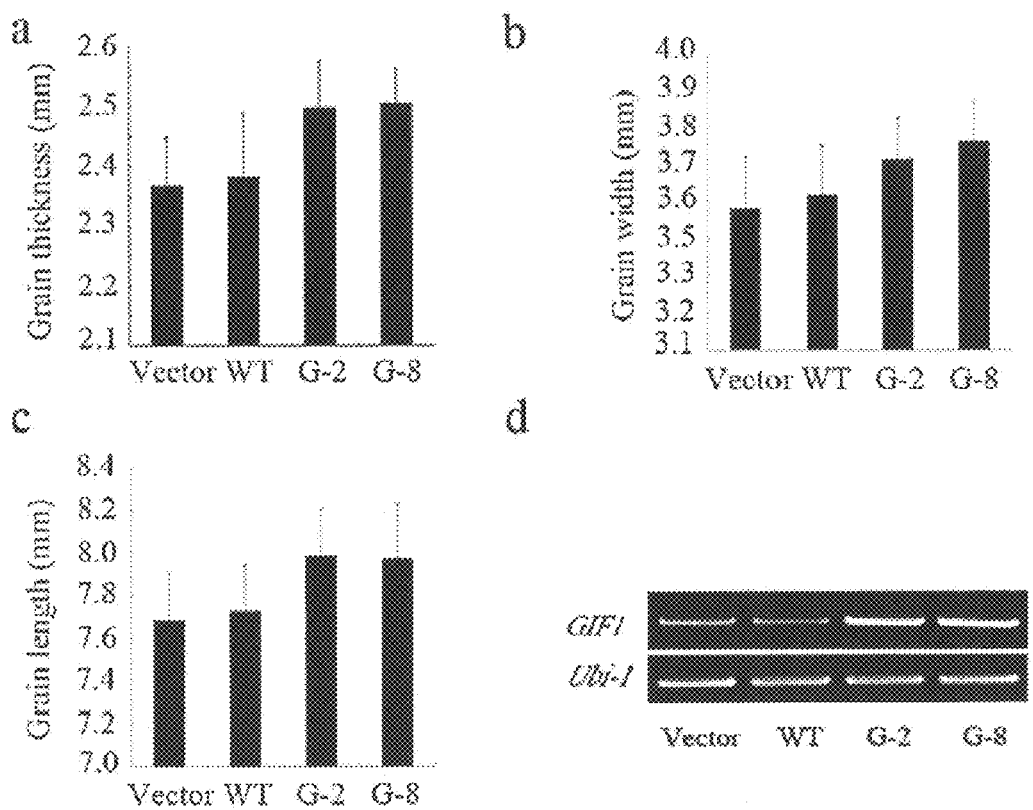
FIG. 9 illustrates that grains of transgenic rice with additional GIF1 show an increase in thickness, width as well as length, and enhanced expression of GIF1. (a-c) two transgenic rice lines of G-2 and G-8 overexpressing GIF1 are compared with wild-type rice (WT) and empty vector transformed rice (Vector) in terms of grain thickness (a), width (b), and length (c). Results confirm that transgenic rice lines of G-2 and G-8 that overexpress GIF1 possess larger grains. (d) two transgenic rice lines of G-2 and G-8 overexpressing GIF1 are compared with wild-type rice (WT) and empty vector transformed rice (Vector) in terms of gene expression level of GIF1 using RT-PCR. Results illustrate that transgenic rice lines of G-2 and G-8 that overexpress GIF1 show higher expression of the GIF1 gene. Ubi-1 refers to the loading control.

Besides, the inventor constructed the recombinant plasmid of pCAMBIA1301-GIF1 containing GIF1 gene, and transformed the same to the calli of wild-type rice (cultivar TP309). Transgenic crop overexpressing GIF1 was obtained, and was compared with the wild-type crop. Results showed that the former possessed bigger and heavier grains as shown by FIGS. 8 and 9 (a-c). mRNAs were extracted from transgenic rice of G-2 and G-8 overexpressing GIF1, wild-type rice (WT), and empty vector transformed rice (Vector) to separately amplify GIF1 through RT-PCR. The amplified product was detected by agarose electrophoresis, and results showed that the transgenic rice overexpressing GIF1 possessed higher expression level of the GIF1 gene (FIG. 9d).

Example 4

Effect of GIF1 Gene on Seed Vigor

Plants with wild-type GIF1 gene showed strong rooting and rapid leaf growth, while plants with mutant gif1 gene showed significantly weak rooting and slow leaf growth. The inventor constructed the recombinant plasmid of pCAMBIA1301-GIF1 containing GIF1 gene, and transformed the same to the calli of the mutant (gif1) to produce the mutant transgenic plant. Rooting and leaf of the transgenic plant could regain the wild-type features.

Figure 2:
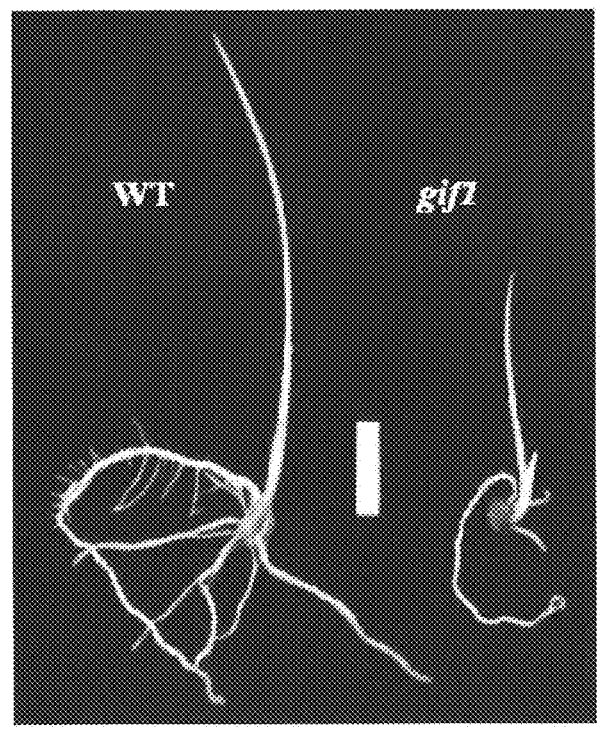
FIG. 2 shows the effect of GIF1 gene on seed vigor, wherein WT (left) refers to ZH11 wild-type plant and gif1 (right) refers to ZH11 mutant plant.

As illustrated in FIG. 2, plants with wild-type GIF1 gene showed strong rooting and rapid leaf growth, while plants with mutant gif gene showed significantly weak rooting and slow leaf growth.

Results demonstrated that the gif1 mutant caused a reduced seed vigor, whereas complementation could effectively eliminate the reduction in seed vigor as induced by the gif1 mutant.

Example 5

Effect of GIF1 Gene on Seed Ear and Resistance to Storage Diseases

The inventor constructed the recombinant plasmid of pCAMBIA1301-GIF1 containing GIF1 gene, and transformed the same to the calli of the mutant (gif1) to produce the mutant transgenic plant. Resistance of the transgenic plant to storage diseases could recover to the wild-type state.

Figure 3:
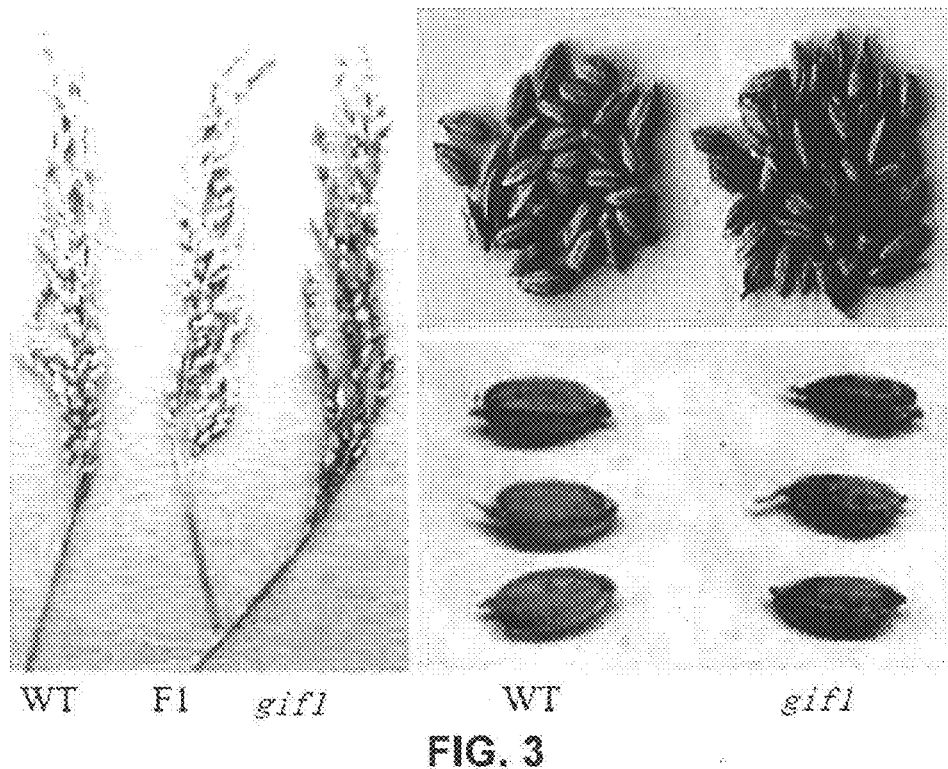
FIG. 3 shows the effect of GIF gene on the crop ear, wherein WT refers to the ear of ZH11 wild-type plant; F1 refers to the ear of the first filial generation of ZH11 wild-type and ZH11 mutant plants; gif1 refers to the ear of ZH11 mutant plant.
Figure 4:
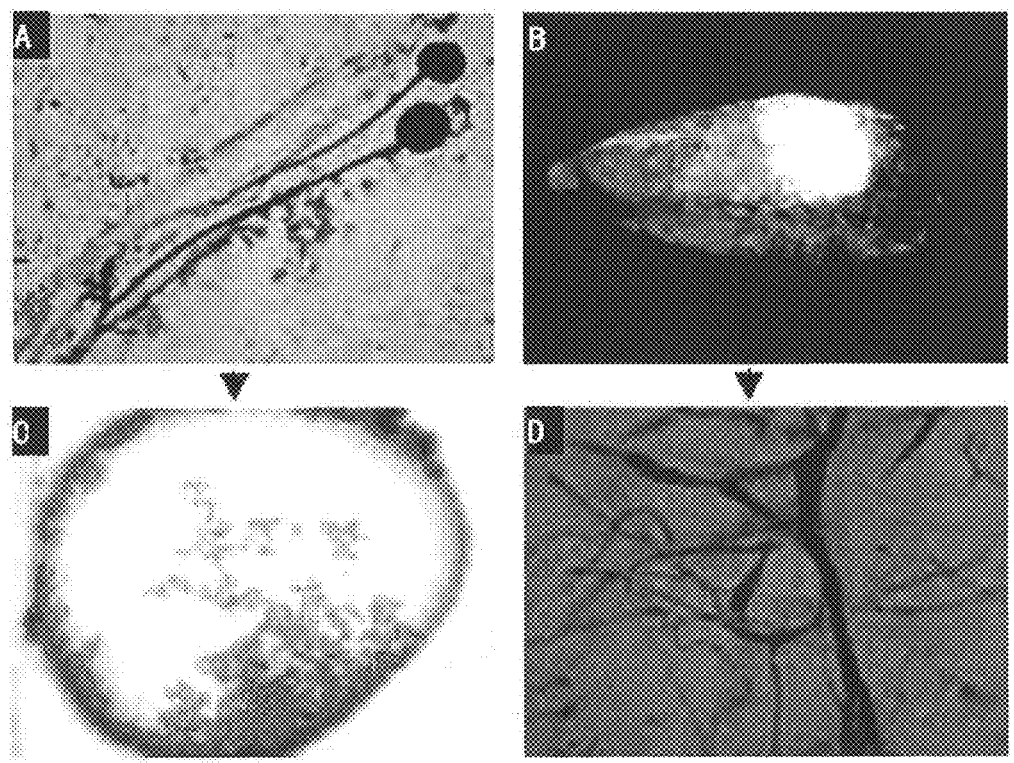
FIG. 4 shows the typical storage disease bacteria isolated from the seeds of gif1 mutant plant, wherein FIG. 4A and FIG. 4C (magnification of FIG. 4A) refer to the isolated *Rhizopus* sp.

Results were shown in FIGS. 3 and 4. As shown in FIG. 3, plants with wild-type GIF gene possessed full ears, while plants with mutant gif gene possessed notably shriveled ears which were more sensitive towards diseases. FIG. 4 showed the typical storage disease bacteria isolated from the seeds of gif1 mutant plant, wherein FIGS. 4A and 4B refer to the isolated *Rhizopus* sp. and *Alternaria* sp., respectively. In addition, some other storage disease bacteria were also isolated.

Results indicated that gif1 mutant reduced ear quality and crop resistance towards storage diseases, thus shortening the storage time. Comparatively, transgenic complementation could eliminate such interference and improve the crop resistance.

Example 6

Tissue Specificity of GIF1 Gene

The inventor constructed a clone comprising GIF1 promoter region operably linked to the GUS reporter gene, and transformed the same to ZH11 rice. Tissue specific expression of the GUS reporter gene and GIF1 gene as promoted by the GIF1 promoter was evaluated. Detailed construction method was as follows:

Promoter of the GIF1 gene was obtained by PCR with forward primer (tataagcttgatcggccatactcc (SEQ ID NO: 4)), reverse primer (taggatccctttgctctcacacttg (SEQ ID NO: 5)), and using the GIF1 genome DNA as template. The promoter was cloned into pBI101 (from Clonetech, bearing GUS), which was then digested by EcoR I and Hind III. The fragment obtained was collected and ligated to equally digested pCAMBIA1300 to produce the desired clone containing pCAMBIA1300+promoter+GUS (method for the tissue coloration assay was described in Jeferenson, R A (1987) Plant Mol Biol Rep).

As shown in FIGS. 5A-K, specific expression of the GIF1 gene was detected in the root, internode, and vascular trace in the dorsiventral region of the seed.

Figure 5:
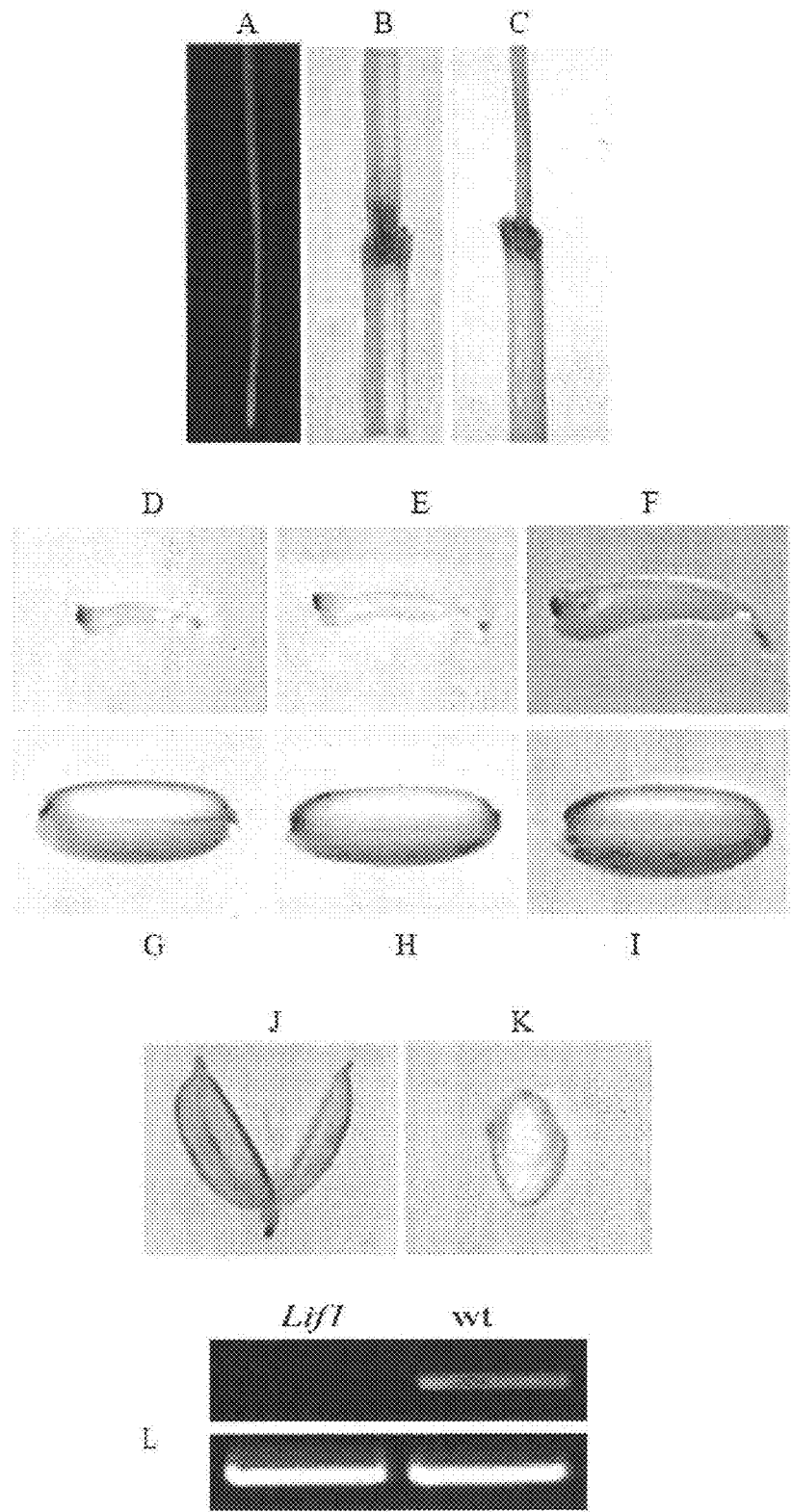
FIG. 5 shows the tissue specificity of GIF1, wherein Fig. A represents root; Fig. B represents internode; Fig. C represents stretched-out (elongated) internode; Fig. D represents the $2^{nd}$ day; Fig. E represents the $4^{th}$ day; Fig. F represents the $6^{th}$ day; Fig. G represents the $10^{th}$ day; Fig. H represents the $15^{th}$ day; Fig. I represents the $25^{th}$ day; Fig. J represents glume; Fig. K represents cross section of seed on the $10^{th}$ day; Fig. L represents the expression of GIF1 gene in mutant and wild-type plants; Fig. M represents the expression of GIF1 gene in seedlings, leaves, roots, internodes, and ears (wherein LS refers to rice seedlings, L to rice leaves, R to rice roots, I to rice internodes, and P to ears); Fig. N represents the expression of GIF1 gene at different time intervals post to flowering; and DAF (Day After Flowering) refers to the number of days post to flowering.
Figure 5:
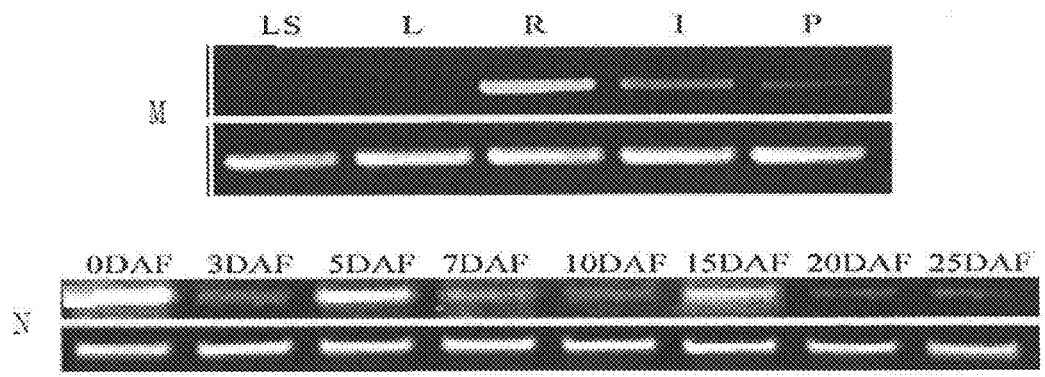

In addition, mRNA was extracted from wild-type or mutant crops, and GIF1 was separately amplified through RT-PCR. The amplified products were detected by agarose electrophoresis. The results were shown in FIGS. 5L-N. FIG. 5L showed the RT-PCR result of mRNA from gif1 mutant and wild-type crops; FIG. 5M showed the RT-PCR result of mRNA from different rice tissues; FIG. 5N showed the RT-PCR result of mRNA from rice ear on different days after flowering (DAF).

Example 7

Effect of GIF1 Gene on Sugar Metabolism and Accumulation in Grains

The inventor constructed the recombinant plasmid of pCAMBIA1301-GIF1 containing GIF1 gene, and transformed the same to the calli of the mutant (gif1) to produce the mutant transgenic plant. Sugar metabolism and accumulation of the transgenic plant was monitored and compared with that of wild-type ZH11 plant.

Figure 6:
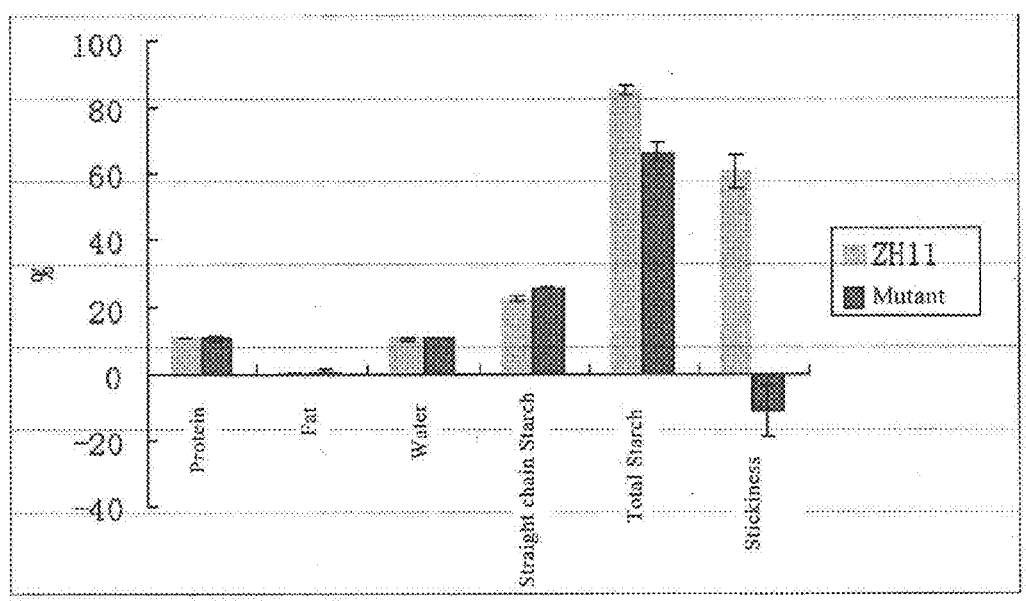
FIG. 6 shows the effect of GIF1 gene on the grain sugar metabolism and accumulation, wherein total starch includes amylose and amylopectin.

As shown in FIGS. 6 and 7 (h-j), GIF1 could successfully regulate sugar metabolism and accumulation in grains, thus regulating grain quality.

All the documents cited herein are incorporated into the invention as reference, as if each of them is individually incorporated. Further, it would be appreciated that, in the above teaching of the invention, the skilled in the art could make certain changes or modifications to the invention, and these equivalents would still be within the scope of the invention defined by the appended claims of the present application.

The invention claimed is:

1. A method for improving a crop, wherein the method comprises:

introducing a crop grain filling gene into the crop, wherein the crop grain filling gene comprises a polynucleotide encoding the crop grain filling protein, wherein the crop grain filling protein is selected from:

(a) a polypeptide having the amino acid sequence of SEQ ID NO: 2; or (b) a conserved variant polypeptide derived from the polypeptide of (a) by substitution, deletion or addition of 1-20 amino acid residues in the amino acid sequence of SEQ ID NO: 2 and having the activity of promoting crop grain filling.

2. A transgenic plant prepared by the method of claim 1.

3. The method of claim 1, wherein the polynucleotide encodes a polypeptide having the amino acid sequence of SEQ ID NO: 2.

4. The method of claim 1, wherein the polynucleotide having a sequence selected from:

(1) a nucleotide sequence of SEQ ID NO: 1;
(2) a nucleotide sequence of SEQ ID NO: 3; or
(3) a nucleotide sequence complementary to the nucleotide sequence of (1) or (2).

5. The method of claim 1, wherein the method comprises the steps of:

introducing the polynucleotide into a plant cell or tissue to produce a transformed plant cell or tissue,
culturing the transformed plant cell or tissue, and
generating a transgenic plant from the transformed plant cell or tissue.

6. The method of claim 5, wherein the introducing uses an Agrobacterium harboring an expression vector.

7. The method of claim 1, wherein the crop is a Gramineous plant.

8. The method of claim 6, wherein the Gramineous plant is one selected from the group consisting of rice, wheat, barley, maize, and broomcorn.

* * * * *

SEQUENCE LISTING

```
<160> NUMBER OF SEQ ID NOS: 5

<210> SEQ ID NO 1
<211> LENGTH: 1797
<212> TYPE: DNA
<213> ORGANISM: Oryza sativa L.

<400> SEQUENCE: 1
atgggagttc ttggtagtag ggtcgcttgg gcatggctgg tccagctgct gctgctccag      60
```

-continued

| | |
|---|---|
| cagctcgccg agcgtcgca cgtcgtctac gacgacctcg agctgcaggc ggctgctacc | 120 |
| acagcggacg gcgtgccgcc gtccatcgtc gactctgagc tccggactgg gtatcacttc | 180 |
| cagccaccca agaactggat caatgatccg aacgcgccga tgtactacaa ggggtggtac | 240 |
| catctgttct accagtacaa ccccaagggg gccgtgtggg ggaacatcgt gtgggcgcac | 300 |
| tcagtgtcac gtgacctcat caactgggtg gcgctcaagc cggccatcga gcccagcatc | 360 |
| agggccgaca gtacggctg ctggtcgggg tcggcgacga tgatggccga cgggacgccg | 420 |
| gtgatcatgt acaccggcgt caaccgcccc gacgtcaact accaggtgca gaacgtggcg | 480 |
| ctgccgagga acgggtcgga cccgctgctg cgcgagtggg tgaagcccgg ccacaacccg | 540 |
| gtgatcgtgc ccgagggcgg catcaacgcg acgcagttcc gcgacccgac caccgcgtgg | 600 |
| cgcggggccg acgccactg gcggctgctc gtcggcagcc tcgcggggca gtcccgcggc | 660 |
| gtggcgtacg tgtaccggag cagggacttc cggcggtgga cgcgcgcggc gcagccgctg | 720 |
| cactcggcgc ccacggggat gtgggagtgc ccggacttct acccggtcac cgcggacggc | 780 |
| cgccgcgagg gcgtcgacac ctcgtccgcc gtcgtcgacg ccgccgcctc ggcgcgcgtc | 840 |
| aagtacgtgc tcaagaacag cctcgacctg cgccggtacg actactacac cgtcggaacg | 900 |
| tacgaccgga aggccgagcg gtacgtgccg gacgaccccg ccggcgacga gcaccacatc | 960 |
| cgctacgact acggcaactt ctacgcctcc aagacgttct acgacccggc gaagcgccgc | 1020 |
| cgcatcctct ggggatgggc caacgagtcc gacaccgccg ccgacgacgt ggccaagggc | 1080 |
| tgggccggaa tccaggcgat tccgaggaaa gtgtggctgg acccaagtgg gaagcaactg | 1140 |
| ttgcagtggc aatcgagga ggtcgagagg ctgagaggga agtggccggt cattctcaag | 1200 |
| gacagggtgg tcaagccagg ggaacacgtc gaggtgaccg gctacaaaac tgcacaggct | 1260 |
| gacgtggagg tgagcttcga ggtggggagc ctggaggcgg cggagcggct ggaccccggcg | 1320 |
| atggcgtacg acgcgcagcg gctgtgcagc gcgcggggcg ccgacgcgag gggcggcgtg | 1380 |
| gggccgttcg gcctgtgggt gctcgcgtcc gcggggctgg aggagaagac cgccgtgttc | 1440 |
| ttcagggtgt tcaggccggc ggcgcgcggc ggcggcgccg gcaagcccgt cgtgctcatg | 1500 |
| tgcaccgacc ccaccaagtc atcgcgcaac ccgaacatgt accagccgac gtttgcaggg | 1560 |
| ttcgttgaca cggacatcac caacgggaag atatctctga ggagcctgat cgacaggtcg | 1620 |
| gttgttgaga gcttcgggc tggaggaaag gcgtgcatcc tgtcgagggt gtacccgtcg | 1680 |
| ctggccatcg caagaacgc gcgcctttac gttttcaata cgggaaggc ggagatcaag | 1740 |
| gtgtcgcagc tcaccgcgtg ggagatgaag aagccggtca tgatgaatgg agcctaa | 1797 |

<210> SEQ ID NO 2
<211> LENGTH: 598
<212> TYPE: PRT
<213> ORGANISM: Oryza sativa L.

<400> SEQUENCE: 2

Met Gly Val Leu Gly Ser Arg Val Ala Trp Ala Trp Leu Val Gln Leu
1               5                   10                  15

Leu Leu Leu Gln Gln Leu Ala Gly Ala Ser His Val Val Tyr Asp Asp
            20                  25                  30

Leu Glu Leu Gln Ala Ala Ala Thr Thr Ala Asp Gly Val Pro Pro Ser
        35                  40                  45

Ile Val Asp Ser Glu Leu Arg Thr Gly Tyr His Phe Gln Pro Pro Lys
    50                  55                  60

Asn Trp Ile Asn Asp Pro Asn Ala Pro Met Tyr Tyr Lys Gly Trp Tyr
65                  70                  75                  80

His Leu Phe Tyr Gln Tyr Asn Pro Lys Gly Ala Val Trp Gly Asn Ile
                    85                  90                  95

Val Trp Ala His Ser Val Ser Arg Asp Leu Ile Asn Trp Val Ala Leu
            100                 105                 110

Lys Pro Ala Ile Glu Pro Ser Ile Arg Ala Asp Lys Tyr Gly Cys Trp
            115                 120                 125

Ser Gly Ser Ala Thr Met Met Ala Asp Gly Thr Pro Val Ile Met Tyr
    130                 135                 140

Thr Gly Val Asn Arg Pro Asp Val Asn Tyr Gln Val Gln Asn Val Ala
145                 150                 155                 160

Leu Pro Arg Asn Gly Ser Asp Pro Leu Leu Arg Glu Trp Val Lys Pro
                165                 170                 175

Gly His Asn Pro Val Ile Val Pro Glu Gly Gly Ile Asn Ala Thr Gln
                180                 185                 190

Phe Arg Asp Pro Thr Thr Ala Trp Arg Gly Ala Asp Gly His Trp Arg
            195                 200                 205

Leu Leu Val Gly Ser Leu Ala Gly Gln Ser Arg Gly Val Ala Tyr Val
    210                 215                 220

Tyr Arg Ser Arg Asp Phe Arg Arg Trp Thr Arg Ala Ala Gln Pro Leu
225                 230                 235                 240

His Ser Ala Pro Thr Gly Met Trp Glu Cys Pro Asp Phe Tyr Pro Val
                245                 250                 255

Thr Ala Asp Gly Arg Arg Glu Gly Val Asp Thr Ser Ser Ala Val Val
            260                 265                 270

Asp Ala Ala Ala Ser Ala Arg Val Lys Tyr Val Leu Lys Asn Ser Leu
            275                 280                 285

Asp Leu Arg Arg Tyr Asp Tyr Tyr Thr Val Gly Thr Tyr Asp Arg Lys
    290                 295                 300

Ala Glu Arg Tyr Val Pro Asp Asp Pro Ala Gly Asp Glu His His Ile
305                 310                 315                 320

Arg Tyr Asp Tyr Gly Asn Phe Tyr Ala Ser Lys Thr Phe Tyr Asp Pro
                325                 330                 335

Ala Lys Arg Arg Arg Ile Leu Trp Gly Trp Ala Asn Glu Ser Asp Thr
            340                 345                 350

Ala Ala Asp Asp Val Ala Lys Gly Trp Ala Gly Ile Gln Ala Ile Pro
            355                 360                 365

Arg Lys Val Trp Leu Asp Pro Ser Gly Lys Gln Leu Leu Gln Trp Pro
    370                 375                 380

Ile Glu Glu Val Glu Arg Leu Arg Gly Lys Trp Pro Val Ile Leu Lys
385                 390                 395                 400

Asp Arg Val Val Lys Pro Gly Glu His Val Glu Val Thr Gly Leu Gln
                405                 410                 415

Thr Ala Gln Ala Asp Val Glu Val Ser Phe Glu Val Gly Ser Leu Glu
            420                 425                 430

Ala Ala Glu Arg Leu Asp Pro Ala Met Ala Tyr Asp Ala Gln Arg Leu
            435                 440                 445

Cys Ser Ala Arg Gly Ala Asp Ala Arg Gly Gly Val Gly Pro Phe Gly
    450                 455                 460

Leu Trp Val Leu Ala Ser Ala Gly Leu Glu Glu Lys Thr Ala Val Phe
465                 470                 475                 480

Phe Arg Val Phe Arg Pro Ala Ala Arg Gly Gly Gly Ala Gly Lys Pro
                485                 490                 495

Val Val Leu Met Cys Thr Asp Pro Thr Lys Ser Ser Arg Asn Pro Asn

```
                500             505             510
Met Tyr Gln Pro Thr Phe Ala Gly Phe Val Asp Thr Asp Ile Thr Asn
            515             520             525

Gly Lys Ile Ser Leu Arg Ser Leu Ile Asp Arg Ser Val Val Glu Ser
        530             535             540

Phe Gly Ala Gly Gly Lys Ala Cys Ile Leu Ser Arg Val Tyr Pro Ser
545             550             555             560

Leu Ala Ile Gly Lys Asn Ala Arg Leu Tyr Val Phe Asn Asn Gly Lys
                565             570             575

Ala Glu Ile Lys Val Ser Gln Leu Thr Ala Trp Glu Met Lys Lys Pro
            580             585             590

Val Met Met Asn Gly Ala
        595

<210> SEQ ID NO 3
<211> LENGTH: 6840
<212> TYPE: DNA
<213> ORGANISM: Oryza sativa L.

<400> SEQUENCE: 3
gcttgatcgg ccatactccg aagcctcctc tgggtgagcc tcctagtgta cgataggaca      60
cgaccacata tatgaacact caacccctga acacacacaa tctttaacat acgcttgtaa     120
gatactctct ccgtctcata aaaaacgaat ctataaccgg atatgatata ttctagtacg     180
atgaatcttg aaaatgtat gtccagattc gtagtactag gatgtgtcac atctggtatt      240
atgttggttt tttataggac ggaggtagta tataggtccc ttaattttt tttaaaaaaa      300 gaggtacact atagacaaat ctatctatta tattattaaa ggaatagaaa aaggagcctc     360
cacgttcgct cttatggtct agaaattctc acattaatca gaaaaaaga aaaaatagag      420 ttcatataga aatacaattt agaaaaagct gaatttcgga attaaaaaaa tgaatattag     480
aagaggagac tagagtccat atagaaatac aatttagaaa tagttgaaat tcggaattaa     540
aaaataagga atattagaag aggagactag agtccatata aaaatacaat taggaaataa     600
ctgatattca gaatttaaaa taagaatat tagaagtaga gtagagagtc catatagaaa      660
tacaattagg aaataataga aattcggaat taaaaataag gaatattaga aatagagtat     720
agagtctata tagaaataca attaagaaaa aaagaaatt cggaattaaa aaataaggaa      780
tattagaaat agagtataga gtctatatag aaatacaatt aagaaaaaaa aatagaaatt     840
cggaattaaa aaatggaat attagaatta gagtatagag tccatatagg aatttaaaac      900
taactaaaat ttgaataaaa cataataaaa ttaaagtaga gtttagagtc cgtataaaaa     960
tacaatttac aaataactaa aattcgagat taagaaaaat atgggaagaa gagtttaaag    1020
tcaatataga aatgcaattt agaagtaact gaaattcgaa attaaaaatt aaagaatatt    1080
gaaagataag tttagagtcc acatagaaat acaattaaaa ataataaaaa ttcagaaata    1140
aaaataaata atattggaag aagagcatag agtctatata gaaatacaat ttacagaaaa    1200
ttcggaatta aaaatatat attaaaagac gagtctagag tgcatatagg aatatatata    1260
atttacaaat aattaaaaat tgatattaaa ataattaata actaacacgt atataaaata    1320
caatatgaat attacccatt agtagtttcg taaagttatt gcaaaattta aaattatatt    1380
gtcaatttaa tatatttgaa caatatattg agaaaacata tatgctatta tatgagagaa    1440
aatataatag ttcatagtga attgtgaaca ctgatttaaa aacaaacaga ttaacaacca    1500
catcgtttgg cttattcgtg gaataagcta aacggcatat ttgcaaacga aaagtaattt    1560
```

```
gtgaataaaa tttttatata cgtgttctta gcaatctaaa atcaaagagt gaaaataaa    1620 cttcgatgaa aaaaacccaa aatcagcttc aaatttaaag ttaaaaattt aagtttagct    1680
gataagtata agtataaacg aaaagatgat gccgtaattt tctagacatg aaagatcaat    1740
agaacggatt gacattttcg taatggcctg tagatagaga tataagccac gagaaggagc    1800
agtgctgctc tcttctttac aagctaactt cagtgttttt atacatgaaa aatcgaattg    1860
atatctttgg gttggttcgg attgataacg atctccattc aacttttgct ttttgtttcc    1920
caatacgtta tagatggctt tgtgctccat gcggtgacca tgttaggaaa aaaaagtata    1980
tggatttagg cttgtttgag ctccagctta taaatcagag ccaatatgaa gacaaatccc    2040
aatatatata tatatatata tatatatata tatatatata tatatatatc                2100
aaaaacatga gagaaacatg caggtcacgg acgtcccagg gcacaaataa tgttaggtcg    2160
tccacacagt aatgcggccc gcccgggcct gccattcttc tgcccttttg tccgactcag    2220
caatctttga aatctcaacg cttaggggaa aaaaaacagc gtcttttcca taatgcatct    2280
cttcaccttc gcagtataaa taggacccccc tctcctctgc tcctgctcat cctcctctcc    2340
tcttctcgct ctcacttctt gtgcccaagt gtgagagcaa tgggagttct tggtagtagg    2400
gtcgcttggg catggctggt ccagctgctg ctgctccagc agctcgccgg agcgtcgcac    2460
gtcgtctacg acgacctcga gctgcaggcg gctgctacca cagcggacgg cgtgccgccg    2520
tccatcgtcg actctgagct ccggactggg tatcacttcc agccacccaa gaactggatc    2580
aatggtaatg tgaactaact gaaatgttgc caacttgcca ttgttcatgc cagaacgccg    2640
gtcaggccgt atgatttgca ggtcataggg caccacttgt ggttgtggat actggataga    2700
tgagcaaagg gaacagagtg ctctgttctt gagaattgag acgcagaatc gtgcagagta    2760
actagtacag ttttgacgac gttgttgtgt agaacatcac ctgaactaaa tggctcaact    2820
tgagtaattt atagtcagag ttgaaaatat tgacatcata gtcatatcaa atgtttggca    2880
cacaacataa attacggaca gtacactaag gcatcagttt ttatgtccat tttgtcgggt    2940
cagctagtag agtcaacgtt agcacccacg cggtcacgct gaaagaagta gcttcagaag    3000
catctcacag taaactactg agagtttgcc atctctttt catgaagctc acacttagtc    3060
ccttcgaact gttaacagat gtactacctt gttctacttt tcttgctaat gattcttgtg    3120
acaaggctta gtcctaaccg gcaattttct tgtgcaatta tttggtgggg gtgtgctctg    3180
ctctacactg tgattgctgc tgcgtcatca acattggaaa cccgcagatc cgaacggtac    3240
gtcgttttcc caccctttat aatatatcct gtcacgaatc tctgtctact agtagtagta    3300
gtagtagtac tagaactttt atgccttgca acttgcaatt tcgttgtacg ggagaggact    3360
gtagttagtg acgcctttca tggtaggatt aaaggttcaa agcacatttt agcacgaaaa    3420
tggtaggcgc actgggactc cacatgcagg cttgcttgtc gaccgtgggg tacctagccc    3480
ctaccacggc tgatgaccac aaagttcaga aaatcttaac ttcctctcag aaagggaatt    3540
agccaaaagt tcacctttt ctcgtacgaa atgaagcatc tatagttcta taattaatcg    3600
tgagcagtgt agagaaaaat gcaatgtaca cgcgcgatta aactgaaatg gtaattgatt    3660
tcaatgtact actaagactg aagatcattt cttgatttgg tgaaactgaa cgggtgcatg    3720
cagcgccgat gtactacaag gggtggtacc atctgttcta ccagtacaac cccaagggcg    3780
ccgtgtgggg gaacatcgtg tgggcgcact cagtgtcacg tgacctcatc aactgggtgg    3840
cgctcaagcc ggccatcgag cccagcatca gggccgacaa gtacggctgc tggtcggggt    3900
cggcgacgat gatggccgac gggacgccgg tgatcatgta caccggcgtc aaccgccccg    3960
```

```
acgtcaacta ccaggtgcag aacgtggcgc tgccgaggaa cgggtcggac ccgctgctgc   4020
gcgagtgggt gaagcccggc cacaacccgg tgatcgtgcc cgagggcggc atcaacgcga   4080
cgcagttccg cgacccgacc accgcgtggc gcggggccga cggccactgg cggctgctcg   4140
tcggcagcct cgcggggcag tcccgcggcg tggcgtacgt gtaccggagc agggacttcc   4200
ggcggtggac gcgcgcggcg cagccgctgc actcggcgcc cacggggatg tgggagtgcc   4260
cggacttcta cccggtcacc gcggacggcc gccgcgaggg cgtcgacacc tcgtccgccg   4320
tcgtcgacgc cgccgcctcg gcgcgcgtca agtacgtgct caagaacagc ctcgacctgc   4380
gccggtacga ctactacacc gtcggaacgt acgaccggaa ggccgagcgg tacgtgccgg   4440
acgaccccgc cggcgacgag caccacatcc gctacgacta cggcaacttc tacgcctcca   4500
agacgttcta cgaccggcg aagcgccgcc gcatcctctg gggatgggcc aacgagtccg   4560
acaccgccgc cgacgacgtg gccaagggct gggccggaat ccaggtaatt aaccgcacgt   4620
cctgactgca tacgtgcatg ccatttacgt gtccaccatg catgctgcca tcttcagata   4680
gtcaatatca ccatatactc cctccgttct aaaatgttta acaccattga cttttttagca  4740 catgtttgac cgttcgtctt attaaaaaaa tatgaaatat ataaaactat atgtatacat   4800
aaaagtatat ttaacaatga atcaaatgat atgaaaagaa caaataatta cttaaatttt   4860
ttgaataaga cgaatggtgt caagtatttt gaaaaaagag agtatatctt aaaagtcaaa   4920
tggaacaaca ctagcagctc aattttgctg gtaatctttg attgaatcgt gtgtttgtga   4980
tgtgatgttt taggcgattc cgaggaaagt gtggctggac ccaagtggga agcaactgtt   5040
gcagtggcca atcgaggagg tcgagaggct gagagggaag tggccggtca ttctcaagga   5100
cagggtggtc aagccagggg aacacgtcga ggtgaccggg ctacaaactg cacaggtatt   5160 ccttttttgca tctgtaattc tgtaaaacta tttttttac cccaaaaggg cattcgaata   5220
aaactgctca cacatccatg gttctgtgca tgacagtagt aattattaat aagttatcct   5280
gtttgttttg ctgtgtcctg gaccgatctt tatcttatct ggcacgcctg aagttgtgtc   5340
cagtgtgcag tgcccactga acaccaccta ctacgtgtgc cgtgtcgctt tcttctcgtc   5400
cccttttacc atctcctgca cactttgctc gtacttaact gatctcactg attctctcgt   5460
catccgcgca tgtcacgtac aacttccagg ttgcagcgtg attagtgcac atatcactaa   5520
gacactaaac aacataatta gagagatagt taaggagctc aattaatgtg ctttgttggt   5580
gacgtacgtg agtaggagct gtgatctctg atagcaagtt taatagtata gctaactact   5640
ggctctaaat tatctatagt caatctaata ataaattcat ataatagtta cctataaaca   5700
tatactaaat aattaataca tggttccaca tgtcatacac atatgcatct taaagtccgt   5760
actataattt gctgtaaatc tatagcttgt tgttttctc tctcctctttt tatctcctcg   5820 atcgaaatgt gtttatagct ggcttatagt gtgctattgt ccctggtctg atgaagtgat   5880
catgcattct gtttggtggg gtgcaggctg acgtggaggt gagcttcgag gtggggagcc   5940
tggaggcggc ggagcggctg gacccggcga tggcgtacga cgcgcagcgg ctgtgcagcg   6000
cgcggggcgc cgacgcgagg ggcggcgtgg ggccgttcgg cctgtggtg ctcgcgtccg   6060 cggggctgga ggagaagacc gccgtgttct tcagggtgtt caggccggcg cgcgcggcg   6120 gcggcgccgg caagcccgtc gtgctcatgt gcaccgaccc caccaagtac gtgcggccttt  6180 tgcactttat cggtgattga tcgcactaca caataaacaa atattgcct tgactccgtt   6240 tactgatttt ttggtatggt gcgtatgcgt gcaggtcatc gcgcaacccg aacatgtacc   6300
agccgacgtt tgcagggttc gttgacacgg acatcaccaa cgggaagata tctctgagga   6360
```

```
                                                             -continued gcctggtacg taataggacc aaattatcgg gaaaaaagga aaatgttgca tgacggtatc    6420
ccgttcggat aaaattatac ctcttaaata ttgtccgata cctaataaat attaattggc    6480
taataaacta tttgaatggg atgatatctt tgaggtatcg tctgatacct atctgatagg    6540
tacctcatag gtatcacctc gtccgaacgg gttactgttt tataacattc atctggaaaa    6600
ggttcataaa ttgtagaata tgttttgata tcttgtgtct ctcttgtgca gatcgacagg    6660
tcggttgttg agagcttcgg ggctggagga aaggcgtgca tcctgtcgag ggtgtacccg    6720
tcgctggcca tcggcaagaa cgcgcgcctt tacgttttca ataacgggaa ggcggagatc    6780
aaggtgtcgc agctcaccgc gtgggagatg aagaagccgg tcatgatgaa tggagcctaa    6840

<210> SEQ ID NO 4
<211> LENGTH: 24
<212> TYPE: DNA
<213> ORGANISM: Artificial
<220> FEATURE:
<221> NAME/KEY: misc_feature
<223> OTHER INFORMATION: primer

<400> SEQUENCE: 4
tataagcttg atcggccata ctcc                                            24

<210> SEQ ID NO 5
<211> LENGTH: 25
<212> TYPE: DNA
<213> ORGANISM: Artificial
<220> FEATURE:
<221> NAME/KEY: misc_feature
<223> OTHER INFORMATION: primer

<400> SEQUENCE: 5
taggatccct ttgctctcac acttg                                           25
```